(12) United States Patent
Higaki et al.

(10) Patent No.: US 7,147,608 B2
(45) Date of Patent: Dec. 12, 2006

(54) BLOOD COLLECTING NEEDLE

(75) Inventors: Yoshio Higaki, Osaka (JP); Kenji Yashiro, Osaka (JP); Satoki Hino, Osaka (JP)

(73) Assignee: Nipro Corporation, Osaka (JP)

( * ) Notice: Subject to any disclaimer, the term of this patent is extended or adjusted under 35 U.S.C. 154(b) by 490 days.

(21) Appl. No.: 10/372,193

(22) Filed: Feb. 25, 2003

(65) Prior Publication Data

US 2003/0163063 A1  Aug. 28, 2003

(30) Foreign Application Priority Data

Feb. 25, 2002 (JP) ............................. 2002-047602

(51) Int. Cl.
- *A61B 5/00* (2006.01)
- *A61B 19/00* (2006.01)
- *B65D 81/00* (2006.01)
- *A61M 5/32* (2006.01)

(52) U.S. Cl. ...................... 600/576; 604/413

(58) Field of Classification Search ............... 600/577, 600/578, 573, 576, 579, 580; 604/403, 240–242, 604/411, 413
See application file for complete search history.

(56) References Cited

U.S. PATENT DOCUMENTS

| | | | | |
|---|---|---|---|---|
| 4,679,571 A | * | 7/1987 | Frankel et al. ............... | 600/577 |
| 4,834,715 A | * | 5/1989 | Hanifl ......................... | 604/192 |
| 5,066,287 A | * | 11/1991 | Ryan ........................... | 604/240 |
| 5,117,837 A | | 6/1992 | Wanamaker et al. ......... | 128/763 |
| 5,133,362 A | * | 7/1992 | Moss ........................... | 600/576 |
| 5,553,625 A | * | 9/1996 | Rao ............................. | 600/576 |
| 5,562,103 A | | 10/1996 | Sak .............................. | 128/763 |
| 6,565,573 B1 | * | 5/2003 | Ferrante et al. .............. | 606/73 |
| 6,989,014 B1 | * | 1/2006 | Justin et al. .................. | 606/73 |

FOREIGN PATENT DOCUMENTS

WO    91/14398 A1    10/1991

\* cited by examiner

*Primary Examiner*—Max F. Hindenburg
*Assistant Examiner*—Michael Apanius
(74) *Attorney, Agent, or Firm*—Kubovcik & Kubovcik

(57) ABSTRACT

A blood collecting needle includes a hub having a hole axially formed therein, a needle tube inserted into the hole of the hub and having a sharp edge on each of the distal end and the proximal end of the needle tube, which respectively project from the hub, and a resilient cap mounted airtightly on the proximal end side of the hub and capable of accommodating a portion of the needle tube and the sharp edge on the proximal end of the needle tube, a small diameter portion being formed on the periphery of the hub, and further a thread portion being formed on the periphery of the hub on a proximal end side of the small diameter portion.

1 Claim, 10 Drawing Sheets

PRIOR ART

PRIOR ART

BLOOD COLLECTING NEEDLE

BACKGROUND OF THE INVENTION

The present invention relates to a blood collecting needle. More specifically, this invention relates to a blood collecting needle in which one end of the needle is stuck in a blood vessel of a subject and another end of the needle is communicated with the inside of a vacuum blood collecting tube to allow the collection of blood in an amount corresponding to a negative pressure inside the vacuum blood collecting tube.

In performing clinical examination, for example, serum examination or blood cell examination, a blood collecting needle 51 as shown in FIG. 1, which comprises a hub 52, a needle tube 53 and a resilient cap 54, is ordinarily used. When the blood collecting needle 51 is rotated in the direction of the arrow shown in FIG. 1, a thread portion 521 of the hub 52 is engaged with a thread portion 551 on a distal end of a holder 55 and the blood collecting needle 51 is set at the distal end of the holder 55. In this state, a blade 531 on the distal end of the needle tube 53 is stuck in a blood vessel of a patient. Then, when a vacuum blood collecting tube (not shown) is inserted from an opening at the proximal end of the holder 55 into the inside of the holder 55, an edge 532 on the proximal end of the needle tube 53 is broken through the proximal end of the resilient cap 54 and then through a rubber stopper of the vacuum blood collecting tube which allows the inside of the blood vessel to communicate with the inside of the vacuum blood collecting tube. In this state, blood in an amount corresponding to a negative pressure inside the blood collecting tube is collected in the blood collecting tube.

However, the conventional blood collecting needle 51 shown in FIG. 1 requires troublesome operations such that whenever the blood collecting needle 51 is attached to or detached from the holder 55, the needle 51 has to be screwed into or out of the holder.

Accordingly, blood collecting tools, wherein a blood collecting needle and a holder are connected with the tools in a one touch operation by a fitting, instead of by screwing (Japanese Patent No. 28589/1989, Japanese Patent Application Laid-Open Nos. 297342/1990, 126630/1996 and 60827/2000, etc.), have been proposed. One of these blood collecting tools is a blood collecting needle 61 comprising a hub 62, a needle tube 63 and a resilient cap 64, and a holder 65 as shown in FIG. 2. The blood collecting needle 61 and the holder 65 are adapted such that a small diameter portion 621 formed on the hub 62 is engaged with a hub attaching and detaching mechanism 651 mounted on a distal end of the holder 65. Both of the attachment of the blood collecting needle 61 to the holder 65 and the detachment of the blood collecting needle 61 from the holder 65 are conducted with one touch by using the hub attaching and detaching mechanism 651.

However, the holder 65 having the hub attaching and detaching mechanism 651 is intended for the blood collecting needle 61 having the small diameter portion 621 as shown in FIG. 2. The blood collecting needle 51 having the thread portion 521 as shown in FIG. 1, instead of a small diameter portion, cannot be attached to the holder 65.

Meanwhile, a holder to which a blood collecting needle provided with a thread portion can be attached with one touch and from which the needle having the thread portion can be detached with one touch is also proposed (Japanese Patent No. 2723105). The holder has a structure that the thread portion of the blood collecting needle is fixed on a needle fixing unit mounted on the holder. The needle fixing unit intended for the needle having the thread portion can fix the needle more strongly than the hub attaching and detaching mechanism 651 shown in FIG. 2 which is intended for the blood collecting needle 61 having the small diameter portion 621. Nevertheless, such a holder having the needle fixing unit intended for the needle having a thread portion cannot certainly fix a needle having a small diameter portion instead of a thread portion.

As stated above, the conventional holder suits the particular type of blood collecting needle. Accordingly, a holder which suits both a blood collecting needle having a small diameter portion and a blood collecting needle having a thread portion has been developed (Japanese Patent Application Laid-Open No. 33509/1998). The holder described in the application comprises two fixing projections for fixing a needle hub of the blood collecting needle. The fixing projections of the holder fit not only the small diameter portion of the needle but also a valley portion of the thread portion of the needle. Therefore, the holder can fix both types of blood collecting needles.

However, such a holder which suits both of these types of blood collecting needles is complicated in structure and high in cost. Further, the force engaging the fixing projections of the holder with the needle is weaker than that of the hub attaching and detaching mechanism 651 of the holder intended for a needle having a small diameter portion and that of the needle fixing unit intended for a needle having a thread portion, and is not enough to fix the blood collecting needle.

SUMMARY OF THE INVENTION

In view of the circumstances described above, the present inventors have developed a blood collecting needle which can be attached to both a holder for a blood collecting needle having a small diameter portion and a holder for a blood collecting needle having a thread portion.

The present inventors have assiduously conducted various investigations for solving the foregoing problems, and have consequently found that a blood collecting needle capable of solving the problems can be provided by forming a small diameter portion on a hub of the blood collecting needle and further forming a thread portion on its proximal end side.

That is, the invention is a blood collecting needle comprising a hub having a hole penetrated therethrough axially, a needle tube inserted into the hole of the hub and having sharp edges on the distal end side and the proximal end side of the needle tube which respectively project from the hub, a resilient cap mounted airtightly on the proximal end side of the hub and capable of accommodating a portion of the needle tube and the sharp edge on the proximal end side of the needle tube, a small diameter portion being formed on the periphery of the hub, and further a thread portion being formed on the periphery of the hub and on a proximal end side of the small diameter portion.

DESCRIPTION OF THE DRAWINGS

The blood collecting needle of the invention is described in detail below by referring to preferable examples shown in the appended drawings. However, the invention is not limited to these descriptions.

DETAILED DESCRIPTION OF THE INVENTION

Figure 1:
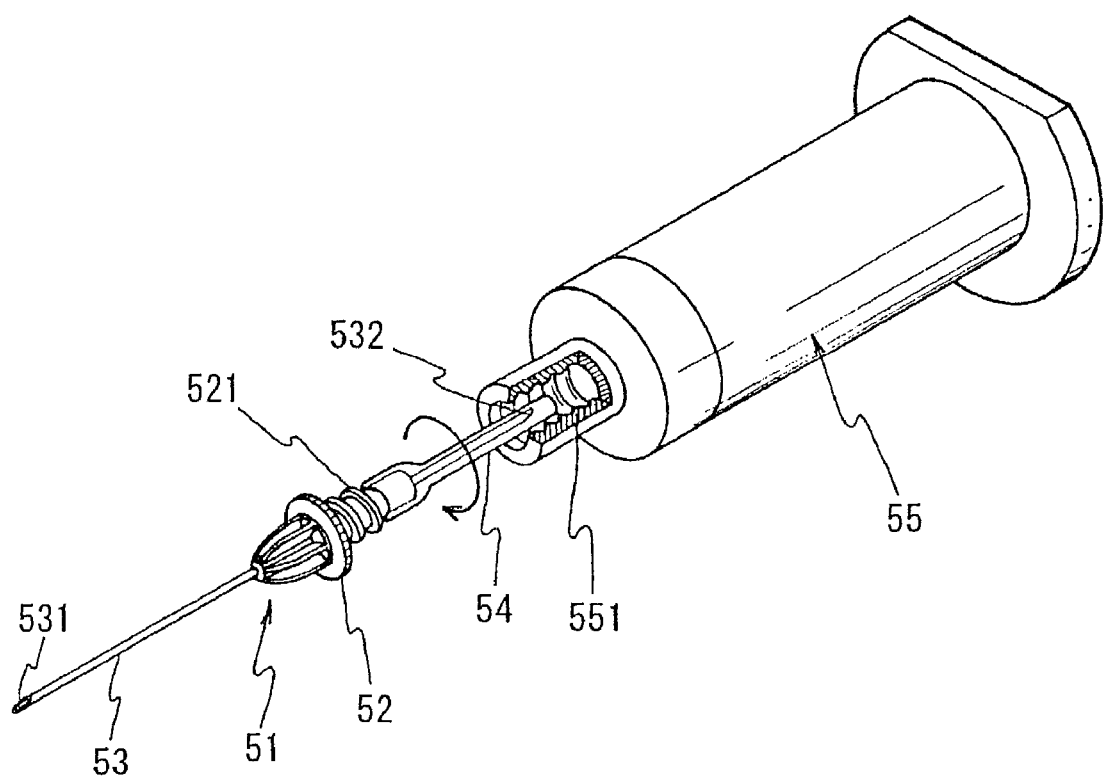
FIG. 1 is a perspective view showing an example of a blood collecting tool intended for an ordinary blood collecting needle having a thread portion.
Figure 2:
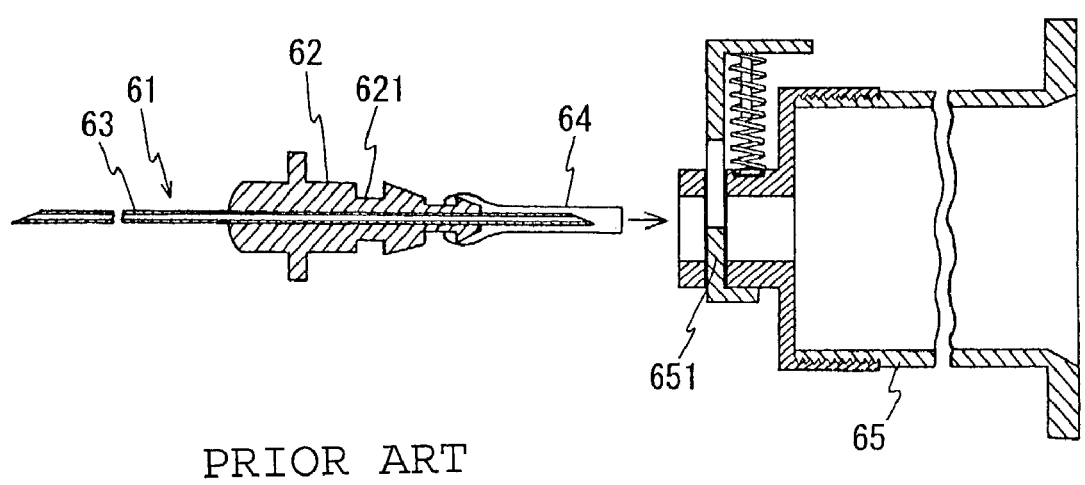
FIG. 2 is a longitudinal sectional view showing an example of a blood collecting tool intended for an ordinary blood collecting needle having a small diameter portion.
Figure 3:
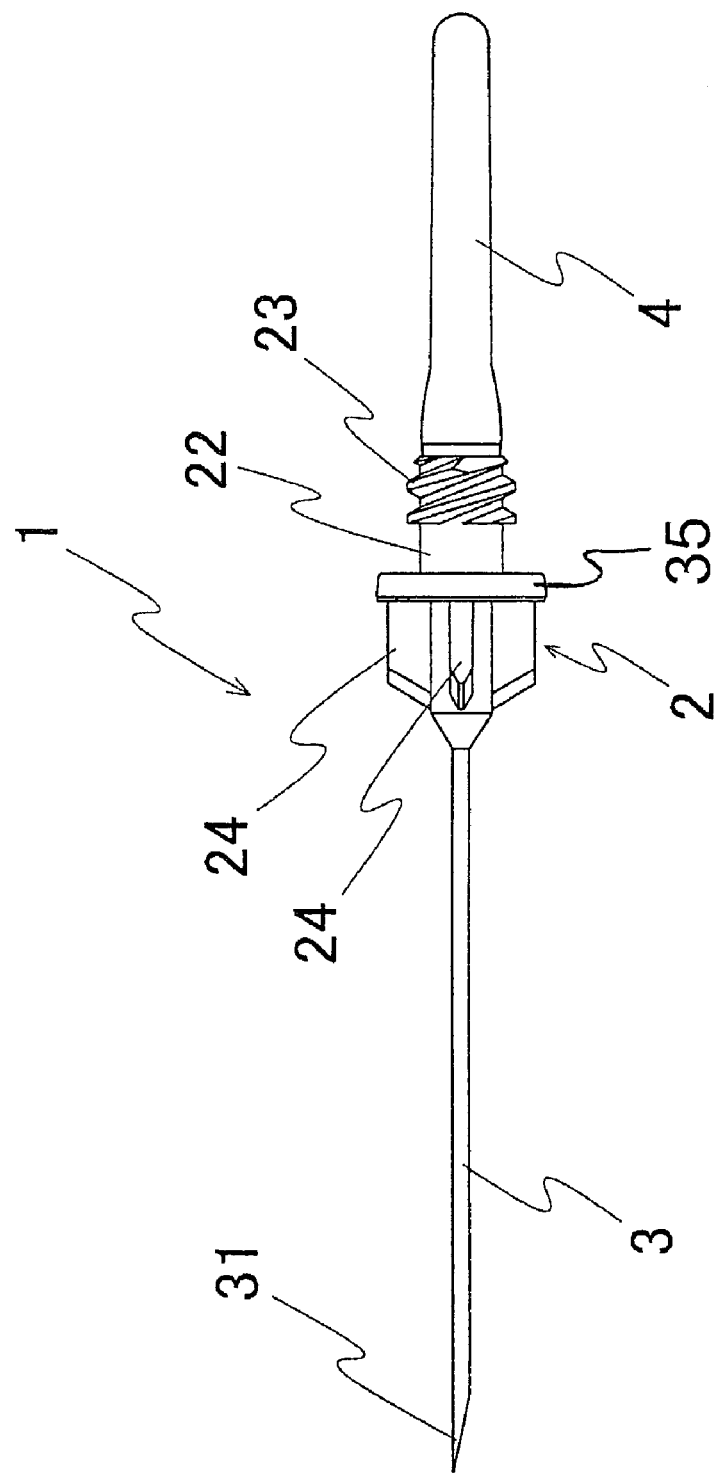
FIG. 3 is a side view showing an example of a blood collecting needle of the present invention.

The blood collecting needle 1 of the present invention has a hub 2, a needle tube 3 which is inserted into a hole formed in the hub and a resilient cap 4 which is mounted on the proximal end side of the hub as shown in FIG. 3.

In the blood collecting needle 1 of the invention, the distal end indicates the end of the needle which is stuck in a patient (left side in FIG. 3), and the proximal end indicates the end of the needle which is stuck in a vacuum blood collecting tube (not shown in the figures) (right side in FIG. 3).

Figure 4:
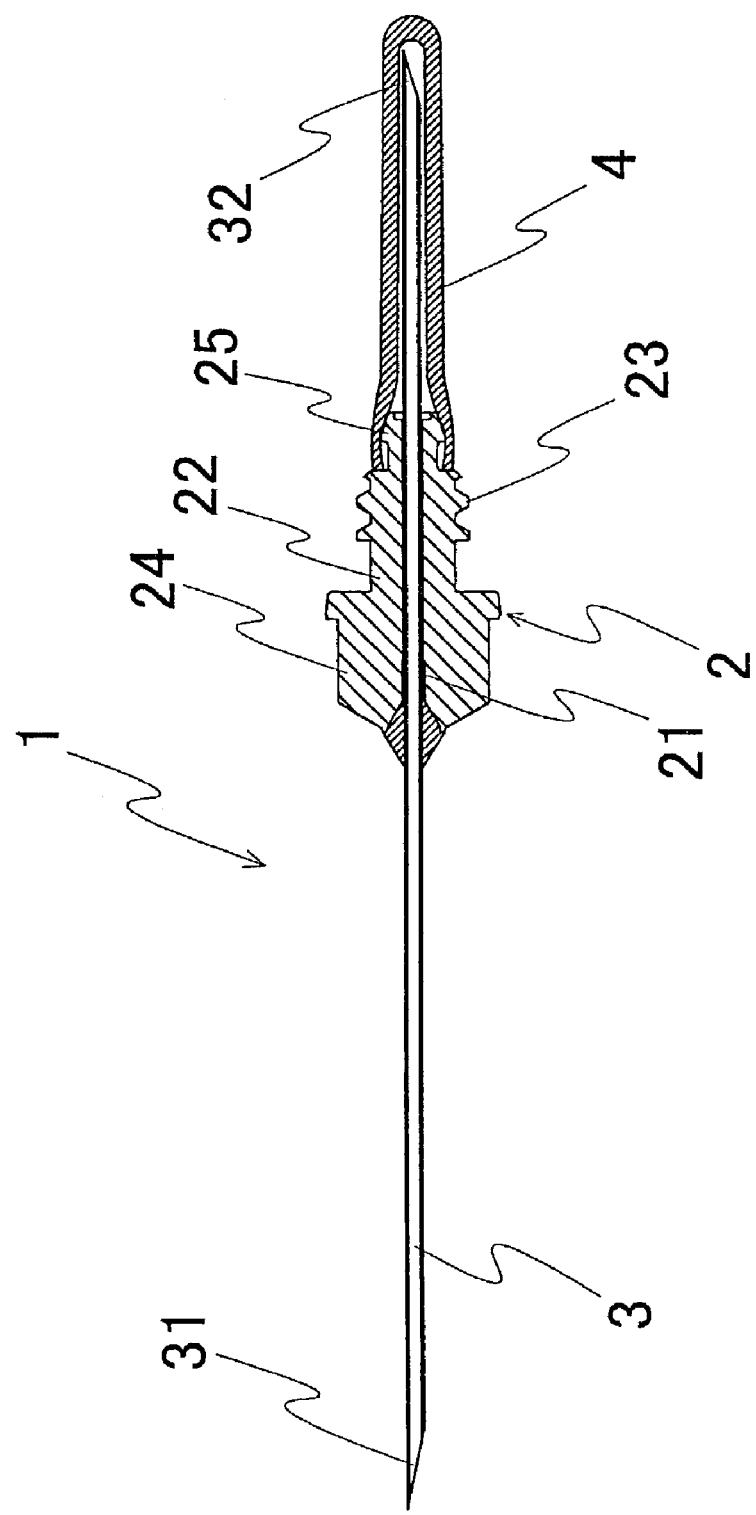
FIG. 4 is a longitudinal sectional view of the blood collecting needle shown in FIG. 3.

As shown in FIGS. 3 and 4, the blood collecting needle 1 of the present invention has a nearly cylindrical hub 2. The hub 2 is a hollow member having a hole 21 formed axially therein. The hole 21 is intended for insertion and fixing of the needle tube 3. An inner diameter of the hub 2 is made slightly larger than an outer diameter of the needle tube 3. The total length of the hub 2 is a length in which the needle tube 3 can be arranged in the hole 21 such that an edge 31 on the distal end portion of the needle tube 3 and an edge 32 on the proximal end portion thereof project from the hub 2.

Figure 5:
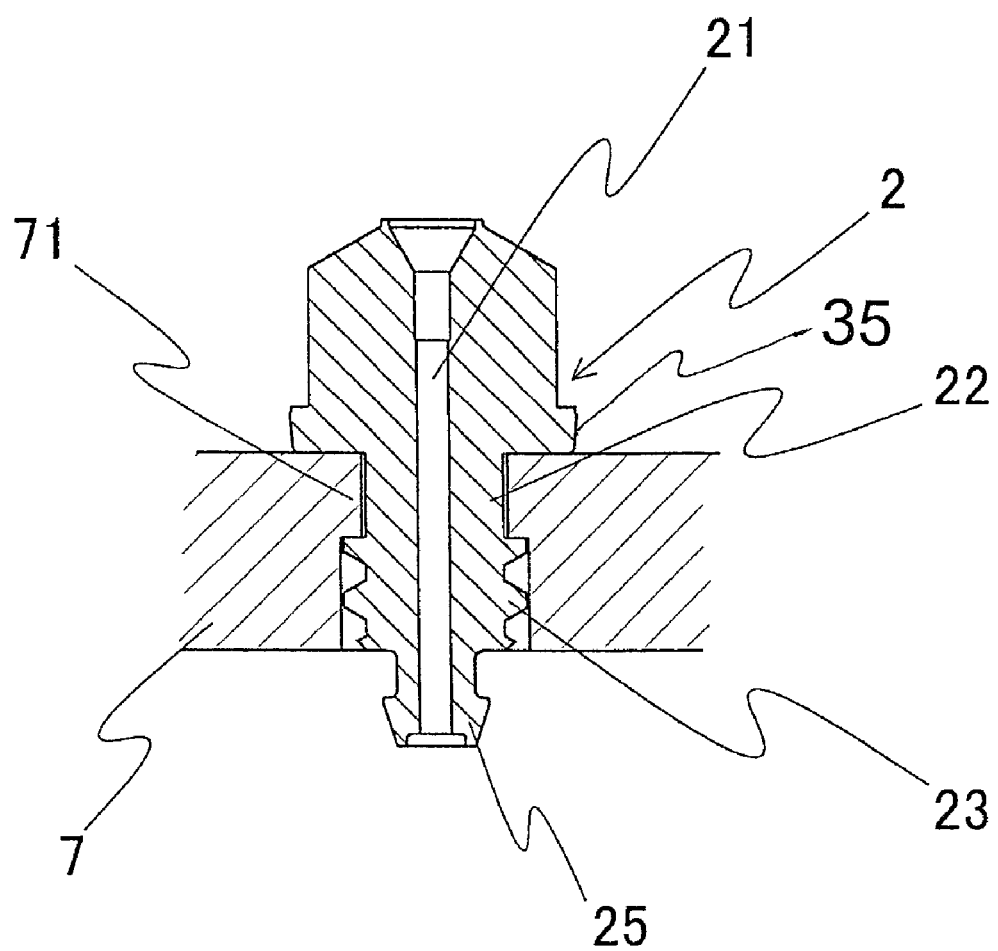
FIG. 5 is a partially enlarged sectional view showing a state where the blood collecting needle of the present invention is fixed on a holder intended for a blood collecting needle having a small diameter portion.

A shoulder portion 35 is provided on the hub 2 intermediate the distal end and the proximal end thereof. The function of the shoulder portion 35 is to prevent the blood collecting needle 1 from moving toward the proximal end of the blood collecting needle 1 and to ensure the fixing of the blood collecting needle 1 when the blood collecting needle 1 is fixed on a holder 7 or a holder 8. A thread portion 23 is formed on the periphery of the hub 2 at the proximal end and a small diameter portion 22 is formed on the periphery of the hub 2 adjacent the thread portion 23 and between the shoulder portion 35 and the thread portion 23. The small diameter portion 22 has a uniform diameter and is a portion which is, when the blood collecting needle 1 is fixed on a holder 7 for a blood collecting needle having a small diameter portion, engaged by a fixing projection 71 of the holder 7 as shown in FIG. 5.

Figure 7:
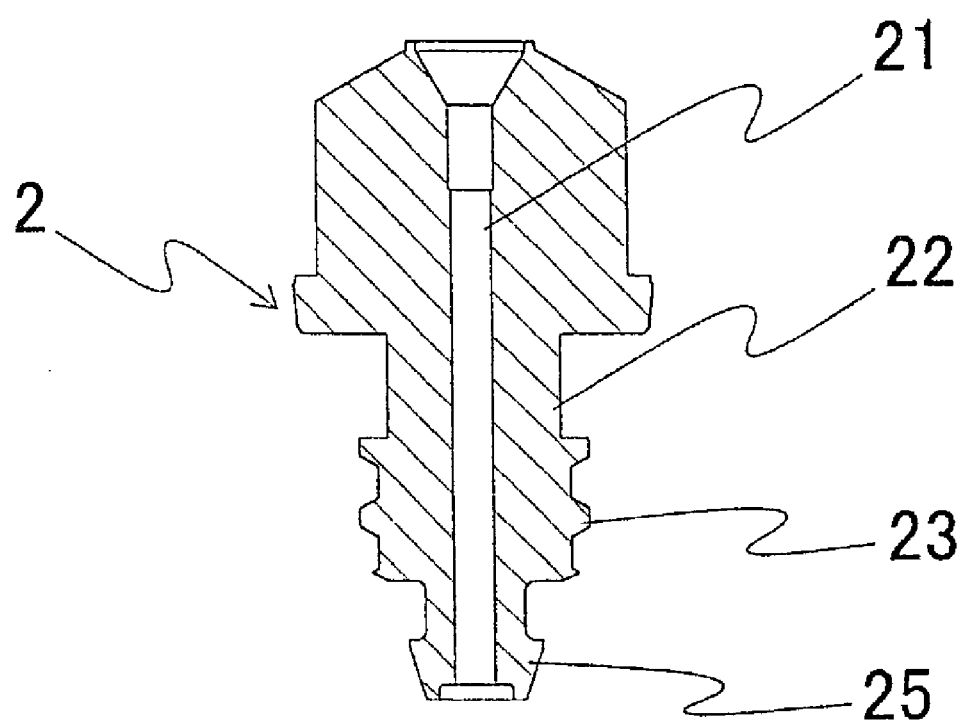
FIG. 7 is an enlarged sectional view showing an example of a hub of a blood collecting needle of the present invention.

The shape and size of the small diameter portion 22 can be changed, as required, according to the shape of the fixing projection 71 of the holder 7. On the other hand, it is preferable that an outer diameter of a valley portion, i.e., minor diameter, of the thread portion 23 in the blood collecting needle 1 is larger than an outer diameter of the small diameter portion 22 for securely fixing to the holder 7 as shown in FIG. 7.

Figure 6:
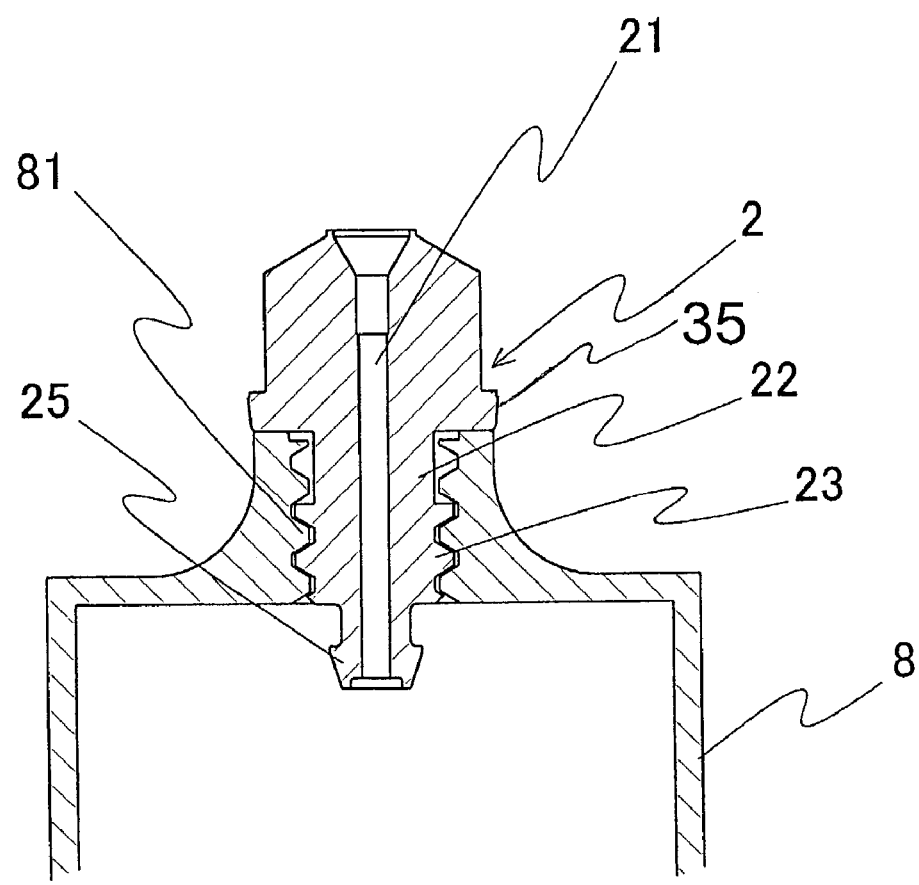
FIG. 6 is a partially enlarged sectional view showing a state where the blood collecting needle of the present invention is fixed on a holder intended for a blood collecting needle having a thread portion.

The thread portion 23 is a portion which is, when the blood collecting needle 1 is fixed on a holder 8 intended for a blood collecting needle having a thread portion, engaged by a fixing projection or an internal thread portion 81 of the holder 8 as shown in FIG. 6. When the holder 8 is of the type that a blood collecting needle 1 cannot be attached to or detached from the holder in one touch, the blood collecting needle 1 can be fixed on the holder 8 by screwing the thread portion 23 into the internal thread portion 81 of the holder 8.

Figure 8:
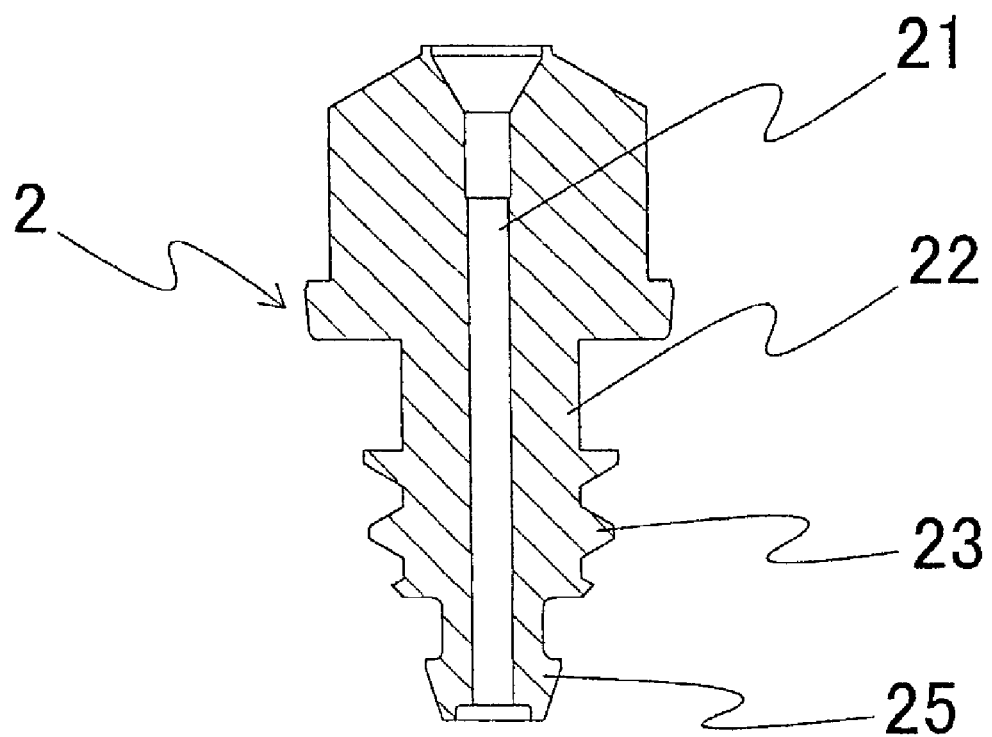
FIG. 8 is an enlarged sectional view showing an example of a hub of a blood collecting needle of the present invention.
Figure 9:
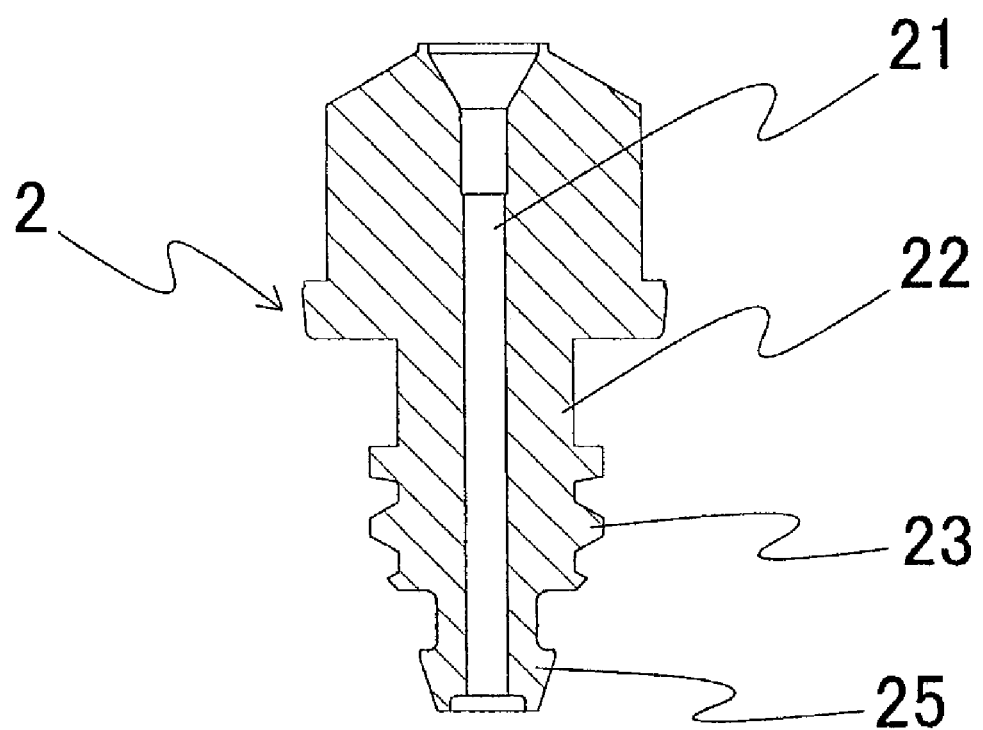
FIG. 9 is an enlarged sectional view showing an example of a hub of a blood collecting needle of the present invention.
Figure 10:
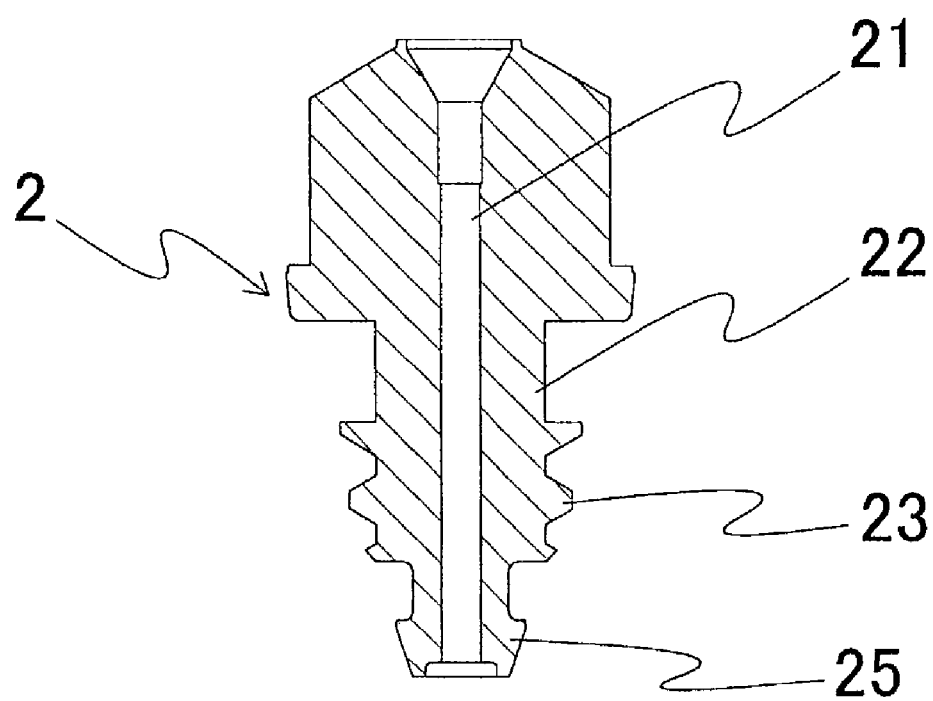
FIG. 10 is an enlarged sectional view showing an example of a hub of a blood collecting needle of the present invention.

The shape of the thread portion 23 can also be changed, as required, according to the shape of the engaging projection or the internal thread portion 81 of the holder 8. With respect to the size of the thread portion 23, it is preferable that an outer diameter of a peak portion, i.e., major diameter, on the distal end of the thread portion 23 is larger than an outer diameter of a peak portion on the proximal end of the thread portion 23 as shown in FIG. 8, a pitch of the thread on the distal end of the thread portion 23 is larger than a pitch of the thread on the proximal end of the thread portion 23 as shown in FIG. 9, or the outer diameter of the peak portion of the thread portion 23 is gradually increased toward the distal end side (upper side in the drawing) for securely fixing the holder 8 as shown in FIG. 10.

Parts required for connection with the holder can further be mounted on the periphery of the hub 2 in the present invention. For example, as shown in FIG. 3 and FIG. 4 at least one rib 24 may be formed on the periphery of the distal end of the hub 2. The rib 24 can be used such that the rib 24 is engaged with a needle cap (not shown) for protecting the needle edge which is stuck in a patient and for preventing rotation of the blood collecting needle 1 within the cap. A stopping portion 25 which can airtightly and detachably fix a resilient cap 4 described later may be formed on the periphery of the proximal end of the hub 2 (refer to FIG. 4).

The hub 2 may have a mechanism capable of confirming a flow of blood into the blood collecting needle 1 upon sticking the edge 31 on the distal end portion of the blood collecting needle 1 in the vein of a subject before sticking the edge 32 on the proximal end portion of the blood collecting needle 1 in the vacuum blood collecting tube, namely, capable of confirming so-called flashback.

Examples of a material suitable for constituting the hub 2 of the present invention include polypropylene, polyethylene, polystyrene, polyethylene terephthalate, polymethylpentene, polycarbonate, polyacrylonitrile, ABS resin, polyvinyl chloride and liquid crystalline polymer. When the hub 2 is provided with a mechanism capable of confirming the flashback, the hub 2 can also be formed of a transparent or translucent material as required.

As a method for forming the hub 2, injection molding or the like is preferably used.

The needle tube 3 is inserted into the hole 21 of the hub 2. The needle tube 3 in the present invention is a hollow tube, and has a sharp edge 31 provided on the distal end portion of the needle tube 3 to be stuck in a patient and a sharp edge 32 provided on the proximal end portion of the needle tube 3 to be stuck in a rubber plug mounted in the vacuum blood collecting tube.

The needle tube 3 is fixed within the hole 21 of the hub 2 such that the edge 31 on the distal end portion extends from the distal end side of the hub 2 and the edge 32 on the proximal end portion extends from the proximal end side of the hub 2. As a method for fixing the needle tube 3 with the hub 2, for example, a method in which the hub 2 is airtightly fixed using an adhesive S is mentioned. As the adhesive S, an epoxy curing agent or a UV-curable adhesive may be used. The adhesive S can be used to fill a part of the clearance between the hub 2 and the needle tube 3. With respect to another example of the fixing method, an ultrasonic or high-frequency fusion or the like is mentioned.

Examples of a suitable material constituting the needle tube 3 include metallic materials such as stainless steel, aluminum, titanium and alloys thereof.

The resilient cap 4 is airtightly mounted on the proximal end of the hub 2. When the hub 2 is provided with the stopping portion 25, the resilient cap 4 is engaged with the stopping portion 25. The resilient cap 4 has a bottomed cylindrical shape, and is formed in such a size that the edge 32 on the proximal end portion of the needle tube 3 can be accommodated in the resilient cap 4. It is preferable that the resilient cap 4 has low penetrating resistance so that the edge 32 on the proximal end portion of the needle tube 3 can easily penetrate the resilient cap at the time of collecting blood and has resiliency such that a hole formed on the proximal end of the resilient cap 4 by penetration of the edge 32 is closed again after the completion of blood collection. Specific examples of the material of the resilient cap 4 include natural rubbers, synthetic rubbers such as isoprene rubber and silicone rubber, and elastomers.

The blood collecting needle 1 is used by sticking the edge 31 on the distal end of the needle tube 3 in the vein of a patient upon fixing the needle on the holder. Subsequently, the vacuum blood collecting tube is inserted into the holder from the proximal end side and the edge 32 on the proximal end of the needle tube 3 is stuck in the resilient cap 4 and the rubber plug of the vacuum blood collecting tube to cause the inside of the blood vessel to communicate with the inside of the vacuum blood collecting tube, whereby blood in an amount corresponding to a negative pressure inside the blood collecting tube is collected in the blood collecting tube.

EFFECT OF THE INVENTION

The blood collecting needle of the present invention can be used without selecting the type of the holder by forming the small diameter portion on the hub of the blood collecting needle and further forming the thread portion on the proximal end side of the small diameter portion. That is, the invention can provide a blood collecting needle which can be installed in both an ordinary holder for a blood collecting needle having a small diameter portion and an ordinary holder for a blood collecting needle having a thread portion. Further, since the blood collecting needle of the present invention is simple in structure, it can be easily manufactured by molding at low cost. Moreover, even when an ordinary holder is used, the blood collecting needle and the holder are securely fixed.

What is claimed is:

1. A blood collecting needle comprising a hub having a hole axially formed therein and having a distal end portion and a proximal end portion, a needle tube having a distal end and a proximal end inserted into the hole of the hub and having a sharp edge on the distal end and a sharp edge on the proximal end which ends respectively project from the distal end portion and the proximal end portion of the hub, and a resilient cap mounted airtightly on the proximal end portion of the hub and capable of accommodating a portion of the needle tube and the sharp edge on the proximal end of the needle tube, wherein the hub has a shoulder portion intermediate the distal end portion and the proximal end portion, a thread portion formed on the periphery of the proximal end portion of the hub, and a small diameter portion formed on the periphery of the hub adjacent the thread portion and between the shoulder portion and the thread portion, and wherein the minor diameter of the thread portion is larger than the diameter of the small diameter portion.

* * * * *